(12) United States Patent
Smith

(10) Patent No.: US 6,623,418 B2
(45) Date of Patent: Sep. 23, 2003

(54) RADIATION SOURCE

(75) Inventor: Leif Smith, Uppsala (SE)

(73) Assignee: Radi Medical Technologies, Inc., Uppsala (SE)

(*) Notice: Subject to any disclaimer, the term of this patent is extended or adjusted under 35 U.S.C. 154(b) by 127 days.

(21) Appl. No.: 09/851,430

(22) Filed: May 9, 2001

(65) Prior Publication Data

US 2002/0026089 A1 Feb. 28, 2002

Related U.S. Application Data

(60) Provisional application No. 60/203,076, filed on May 9, 2000.

(51) Int. Cl.[7] ................................................ A61N 5/00
(52) U.S. Cl. ........................ 600/3; 600/1; 600/400; 600/427; 378/64; 378/145; 378/137
(58) Field of Search .................... 600/1–8, 407, 600/427; 378/64–65, 108, 116, 62, 145, 119, 121, 137–138, 110, 112

(56) References Cited

U.S. PATENT DOCUMENTS

| | | | | |
|---|---|---|---|---|
| 4,472,828 A | * | 9/1984 | Ferlic | .......................... 378/147 |
| 5,630,426 A | * | 5/1997 | Eggers et al. | ................. 128/734 |
| 5,816,999 A | * | 10/1998 | Bischoff et al. | ................ 600/3 |
| 6,287,249 B1 | * | 9/2001 | Tam et al. | ....................... 600/3 |
| 6,319,188 B1 | * | 11/2001 | Lovoi | ............................. 600/3 |

FOREIGN PATENT DOCUMENTS

| | | |
|---|---|---|
| WO | 97/07740 | 3/1997 |
| WO | 98/36796 | 8/1998 |

* cited by examiner

*Primary Examiner*—Teresa Walberg
*Assistant Examiner*—Shawntina Fuqua
(74) *Attorney, Agent, or Firm*—Foley & Lardner

(57) ABSTRACT

A miniaturized radiation device, having a support member in the form of a flexible sheet, and a circuit pattern of electrical contact pads and interconnecting conductor lines or leads provided on said support member. The pads are interconnected via said patterned lines. There is also a plurality of radiation chips electrically connected to selected ones of said pads. Preferably the device is wrapped around a core member, that may be a wire, such that the assembly is suitable for the insertion into a living body for the controlled administration of radiation at a therapy location.

21 Claims, 7 Drawing Sheets

RADIATION SOURCE

Applicant hereby claims the benefit of priority and incorporates the entire contents herein by reference of U.S. Provisional Application Serial No. 60/203,076, filed May 9, 2000.

FIELD OF THE INVENTION

The present invention relates to apparatus and methods for the therapeutic application of ionizing radiation as for example treatment of stenosis in coronary vessels, and in cancer therapy. In particular it relates to a guide wire assembly having an integrated ultra miniature radiation source.

BACKGROUND OF THE INVENTION

The generation of X-rays are commonly achieved by employing X-ray tubes. However, this type of device is expensive, in particular when it is to be adapted for use in very small volumes, i.e. when it is necessary to miniaturize the device substantially.

A much simpler way of manufacturing very small X-ray generating devices is to base the manufacture on chip technology. However, this approach will yield essentially flat devices emitting radiation basically in one direction, at least they will not be capable of emitting isotropic radiation.

In our International Patent Application WO 98/36796 (with priority from pending U.S. application Ser. No. 08/805,296) there is disclosed a miniaturized radiation source which can be energized and de-energized at the site of therapy inside the body at the location of e.g., a tumor to be treated. The radiation source is preferably mounted on a guide wire or a catheter assembly, so as to be easily insertable in the body of a cancer patient.

In WO 97/07740 there is disclosed an X-ray catheter which is said to be usable for irradiation of the site of an angioplasty procedure to prevent restenosis and other conditions in any vessel, lumen or cavity of the body. The device disclosed therein cannot be batch manufactured in the same way as a X-ray emitting chip according to the invention which is the subject matter of the present application, but it irradiates evenly, i.e isotropically.

However, this may also be a disadvantage in the sense that also healthy tissue may become irradiated.

SUMMARY OF THE INVENTION

Thus, it would be desirable to have access to a device for providing ionizing radiation to a therapy location having better efficiency, in terms of capability to irradiate larger areas of the tissue to be treated, in particular to be able to deliver essentially isotropic radiation. It would also be desirable to be able to control the intensity distribution over the damaged or malignous tissue.

Therefore, it is an object of the present invention to provide a device that meets the above requirements and that does not exhibit the drawbacks associated with the prior art devices.

This object is achieved with a device as defined in claim 1, namely with a device for providing ionizing radiation at a therapy location inside a living body, comprising a core member; a flexible support member provided on the surface of said core member; a plurality of miniaturized sources of ionizing radiation attached to said flexible support member; and coupling means for coupling said sources of ionizing radiation to an external power source.

By using a number of X-ray sources together with a selective control for each source, the radiation may be controlled so that it only radiates in selected directions. Thereby it is possible to selectively irradiate desired parts of a vessel or malignant tissue according to the clinical need.

In this way, the individual sources will each contribute to the radiation so as to create an essentially isotropic radiation source. Alternatively, by selectively activating one or more chips, it will be possible to irradiate the parts of the tissue that are malignous thereby avoiding irradiating healthy tissue.

The invention will now be described with reference to the attached drawings.

DETAILED DESCRIPTION OF PREFERRED EMBODIMENTS

Figure 1A:
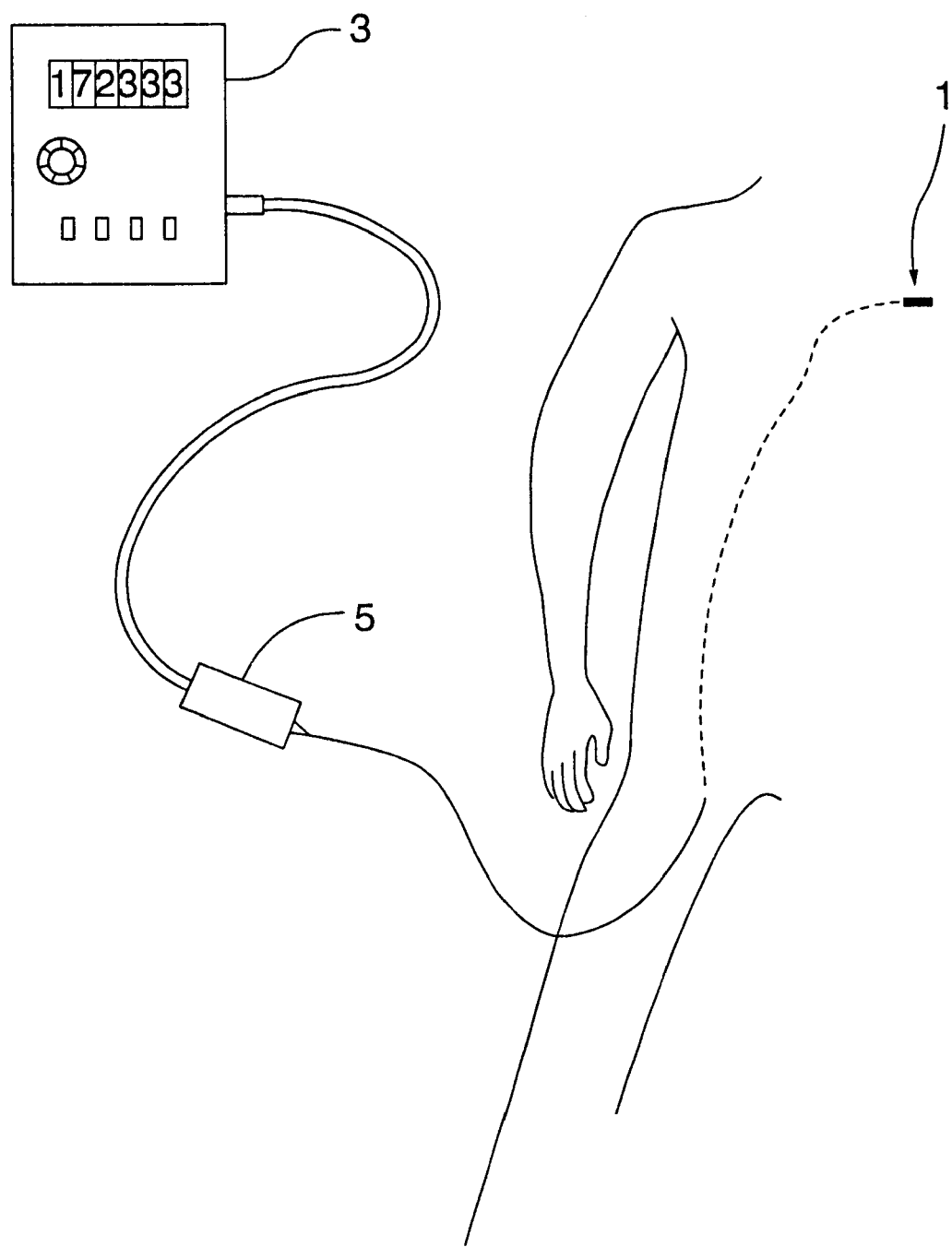
FIG. 1a shows a radiation source according to the invention used together with a guide wire.

FIG. 1a illustrates a system for providing X-ray radiation to a therapy location in a patient. It comprises a radiation source according to the invention provided in the distal region of a guide wire 2 (or a catheter). It also comprises a control unit 3 having the necessary power supply and switching means for selectively energizing and de-energizing the source. The guide wire comprises the necessary electrical leads for coupling the guide wire to the power source, suitably via a connector 5.

Figure 1B:
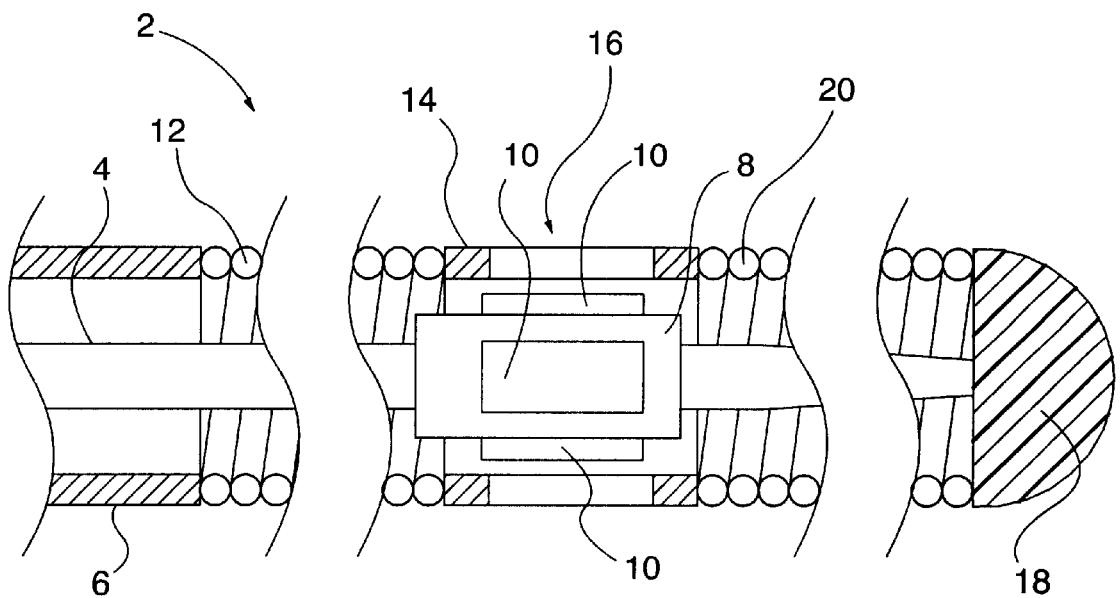
FIG. 1b shows a first embodiment of the radiation device.
Figure 1C:
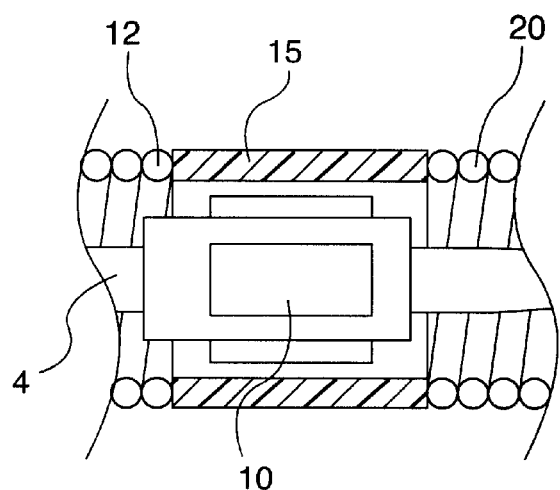
FIG. 1c is an alternative embodiment of the radiation device wherein a polymer is used as a protective X-ray window for the radiation source.

In FIGS. 1b and 1c there is shown a schematic side view, partly in section, of the distal end portion of a guide wire assembly 2 having a miniaturized radiation source according to the present invention attached thereto. In the shown embodiment there is a core wire 4 enclosed in a protective tube 6 (shown in section for clarity), normally made of stainless steel. To the tube 6 there is attached a coil 12 for making the distal end portion of the assembly more flexible. The core wire 4 extends out of the tube 6 but inside the coil 12. Around said core wire 4 about 1–5 mm from the end of said tube 6, there is wrapped a flexible sheet 8 having a plurality, e.g. four, discrete chips 10, capable of providing ionizing radiation when appropriately energized, mounted thereon. The chips are coupled to an external power source (not shown) by electrical leads (not shown). The assembly of flexible sheet and chips provide a radiation device for selectively providing ionizing radiation. The coil 12 ends just before the point of attachment of said flexible sheet, carrying the radiation chips 10. Instead there is mounted a protective piece of tubing 14, 15 around the radiation source. This piece of tubing 14, 15 can be made of any suitable material that adequately protects the chips, and does not hinder the radiation from reaching its target tissue. It can be made of some polymer material 15 (see FIG. 1c), poly-imide being one suitable selection, or of metal 14 (FIG. 1b). Many materials are transparent to X-rays, but if the absorption of X-rays in the material is significant, there should be provided apertures 16 in the tubing in order that the radiation not be stopped from reaching its target.

The core wire 4 extends further in the distal direction and ends in an end plug 18. The core wire is enclosed by a second coil 20 connecting the tube segment 6 and the plug 18.

Figure 1E:
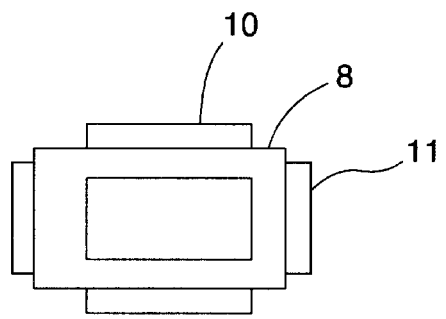
FIG. 1e shows a fourth embodiment of the radiation source where the flexible foil with radiating chips is mounted on a rigid support member of approximately equal length as the flexible support itself
Figure 1D:
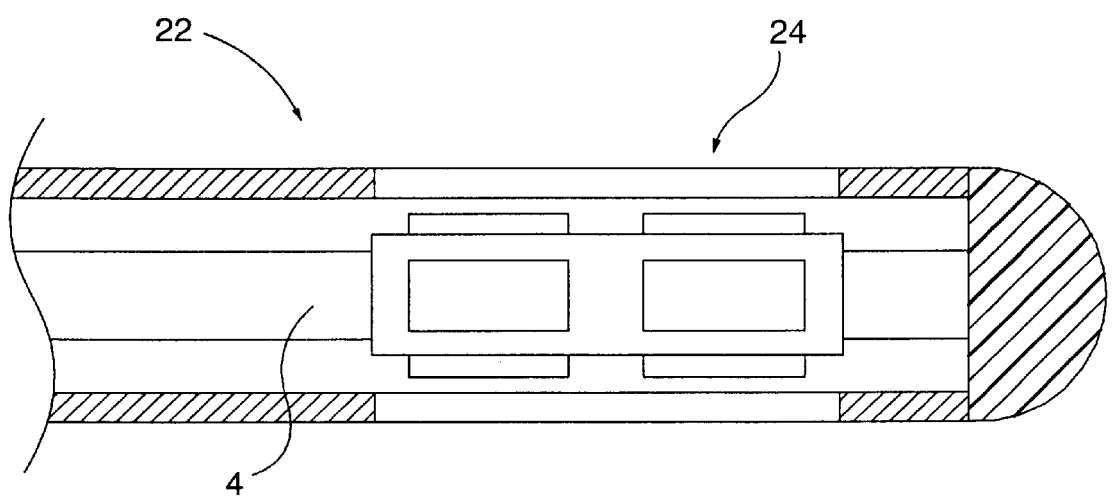
FIG. 1d shows a third embodiment of the radiation device wherein the radiation source is mounted in a catheter.

FIG. 1d illustrates schematically an embodiment where the radiation device is mounted in a catheter 22. In this case there are no coil structures at the distal end. The catheter can be made of any material having appropriate flexibility and being transparent to the radiation, e.g. polyimide or Kapton®.

In the embodiments disclosed in FIGS. 1a–c the flexible sheet or support member 8 is attached onto the surface of a core wire 4. However, the radiation source can equally well be provided on a support element 11 having just about the same extension longitudinally as the flexible support itself, as shown schematically in FIG. 1e. Thus for the purpose of the invention it suffice to attach the flexible support 8 provided with radiation chips 10 on a "core member", which shall be taken to encompass any member capable of providing a sufficiently rigid support for said flexible member.

Figure 2A:
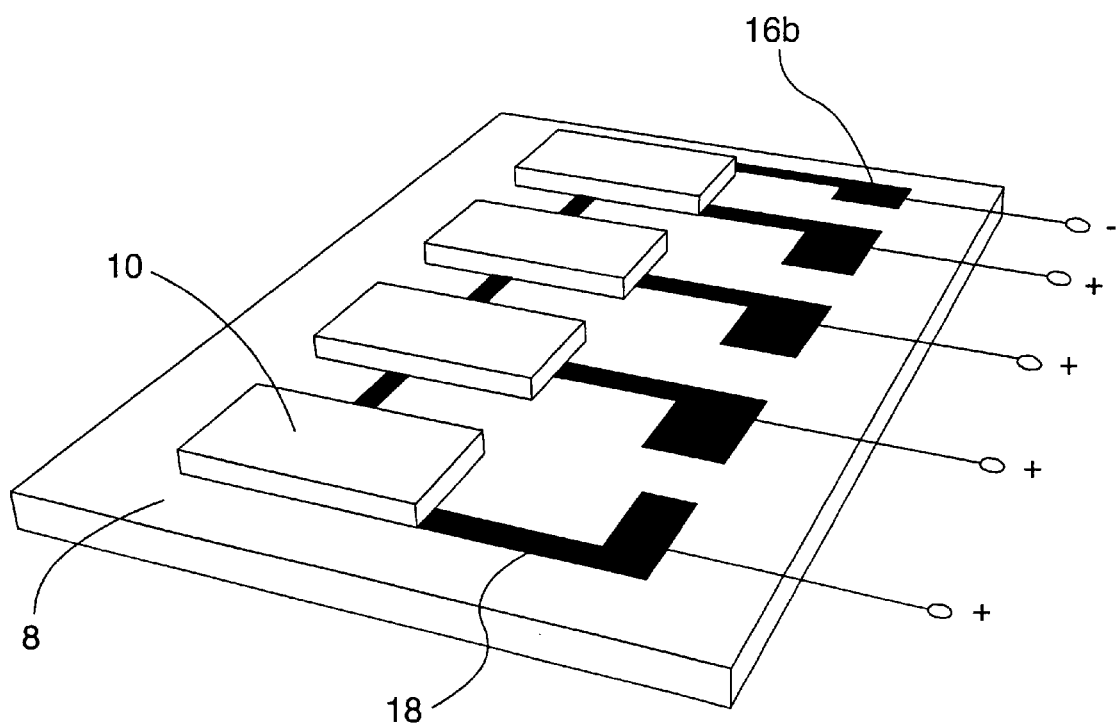
FIG. 2a is a perspective view of a flexible circuit board having a plurality of radiation chips attached to the surface, the circuit board being shown in a flat state before mounting in a guide wire assembly.
Figure 2B:
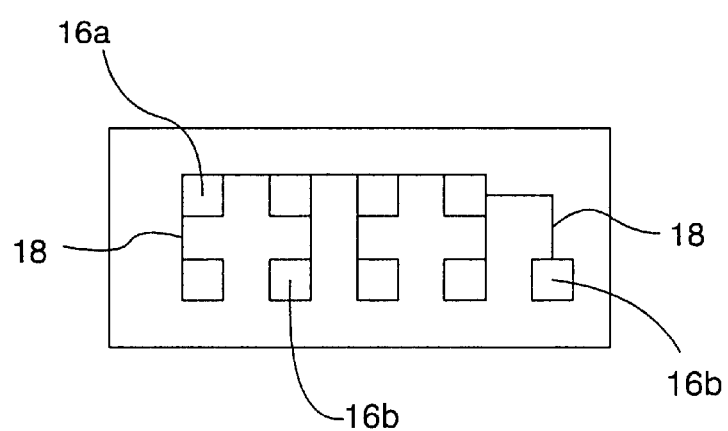
FIG. 2b is a top view of the conductor line lay-out for the circuit board of FIG. 2a showing the difference between pad connecting the X-ray chips to the flexible circuit board and the pads connecting the flexible circuit board to the energizing unit.

In FIG. 2a there is shown in a perspective view a preferred embodiment of the miniaturized radiation device according to the invention in flat form. There is provided a support member 8 in the form of a flexible sheet of a material such as polyimide/kapton. This is the type of material that is commonly used for printed circuits. On this support member 8 there is provided by standard photo lithographic techniques a circuit pattern of electrical contact pads 16 and interconnecting conductor lines or leads 18. This pattern is more clearly illustrated in FIG. 2b. One set of pads 16a are for the purpose of electrically connecting the radiation chips 10, e.g. by bonding or soldering. The other set of pads 16b are intended for the attachment of electrical leads coupling the chips 10 to the external power source mentioned previously. The pads 16a and 16b are interconnected via said patterned leads 18. In this embodiment all chips could be individually energized at a desired voltage, thereby making it possible to create a radiation intensity profile over the circumference. This could be desired if the tissue to be treated is only located to one side in a vessel, and the side where the tissue need not be treated can be protected from being irradiated by simply not energizing the chips on that side.

Figure 2C:
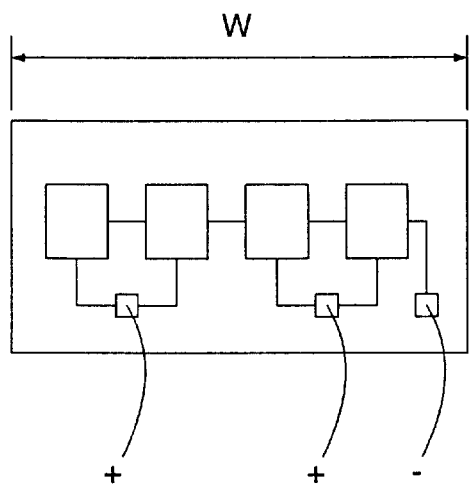
FIG. 2c shows another way of connecting the X-ray chips.

Other circuit patterns are conceivable depending on how it is desired to energize the chips. Thus, as shown in FIG. 2c, the chips can be grouped together such that two or more chips are connected to one voltage source, and another group to a second voltage source.

Figure 2F:
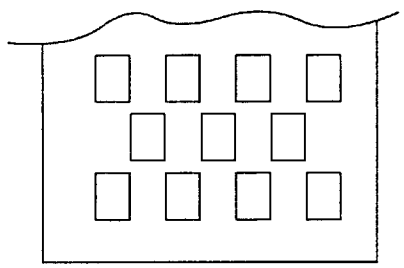
FIG. 2f is yet another way of arranging the X-ray chips to enhance radiation uniformity.
Figure 2D:
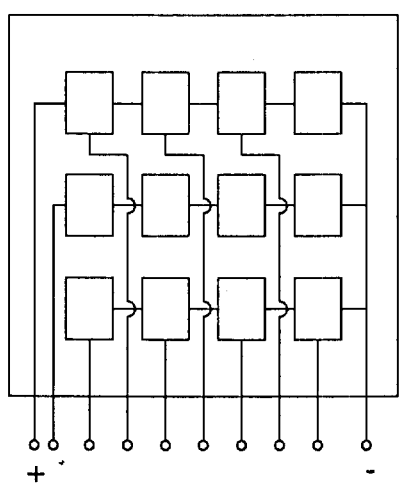
FIG. 2d shows an embodiment wherein the longitudinal radiation profile can be controlled.

Furthermore, as shown in FIG. 2d, there could be several rows of chips on the circuit board. This lay-out enables an irradiation profile to be created in the longitudinal direction of the damaged tissue. The latter design requires a large number of leads.

Figure 2E:
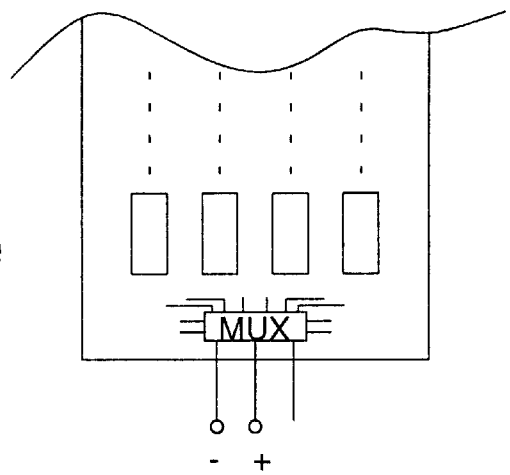
FIG. 2e shows an example of integrating more intelligence on the radiating device by using a MUX.

Instead of providing a plurality of leads, it is conceivable to provide a multiplexer MUX on the flexible circuit board, as shown in FIG. 2e. Thereby it will be necessary with only two excitation/energizing leads and one data line to control the excitation of all chips. Of course in this embodiment the chips would necessarily have to be energized sequentially. This should not be a significant drawback. The only effect is that the duration of the therapy may be somewhat increased.

In still another variation of the actual lay-out of the chips 10, they could be arranged in a staggered fashion, as shown in FIG. 2f. Here there is provided a first row of four chips and a second row of three chips, followed by a third row of four chips.

Figure 2G:
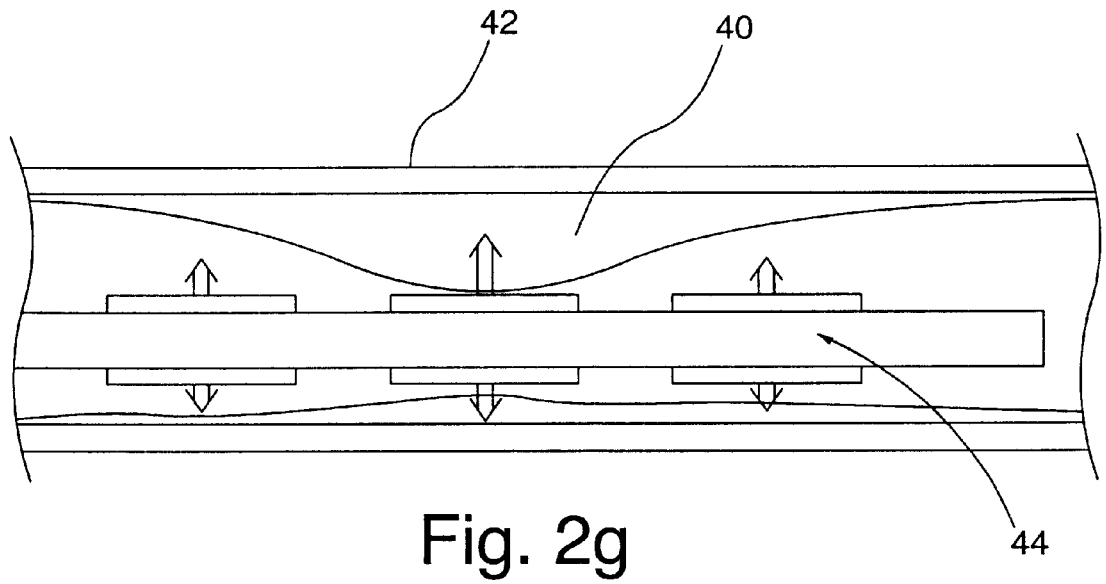
FIG. 2g illustrates the need for achieving a radiation profile in the longitudinal direction.
Figure 4:
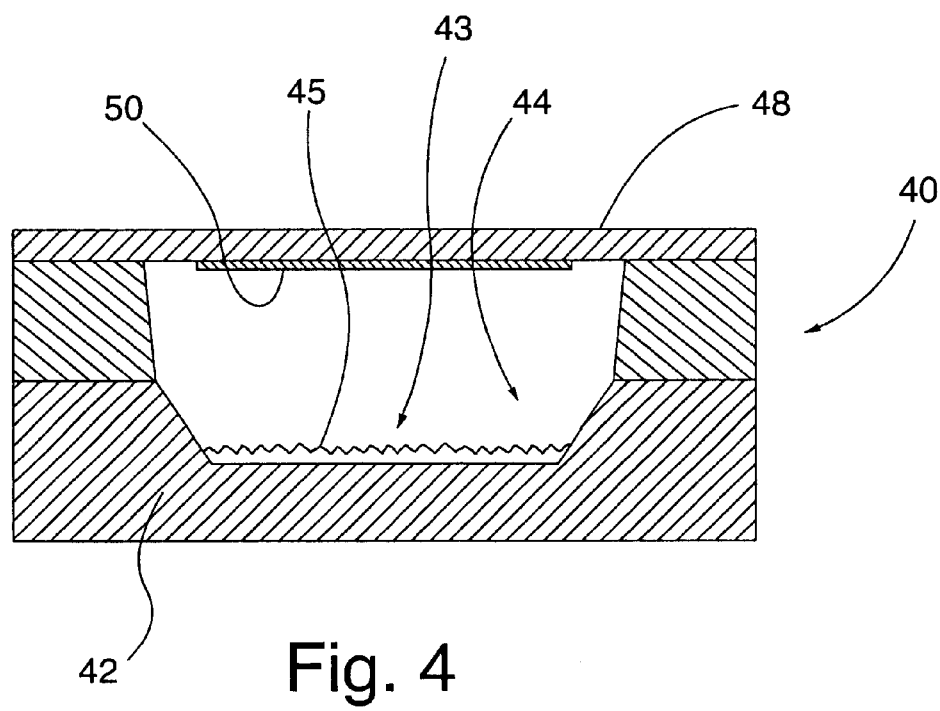
FIG. 4 is a schematic view in cross section of an alternative radiation chip.

By providing a plurality of independently and selectively energizable radiation sources, it is possible to tailor the irradiation profile both longitudinally and circumferentially of the guide wire. This is of particular utility where the stenosis has a longitudinal extension in the vessel, and where it has varying thickness over its length, such that it has a thicker mid-portion, as shown schematically FIG. 2g. In this case the stenosis 40 is asymmetric and has a major part of it located to one side of the vessel 42, and a thicker "waist". The radiation device 44 is programmed to generate radiation having an intensity profile as illustrated with the magnitude vectors (double arrows).

In order to determine the desired dosage profile, an image of the stenosis must first be obtained. This can be done in several ways known per se, e.g. by ultasonic techniques or by X-ray techniques. Once an image of the profile has been obtained, the profile data, i.e. the topology of the stenosis to b treated, is fed into the control unit where it is translated into a dosage profile. Thereafter the control unit will be able to generate a treatment scheme comprising energizing the radiation chips in an appropriate manner in terms of radiation intensity, duration and the sequence of chips to be activated.

Figure 3A:
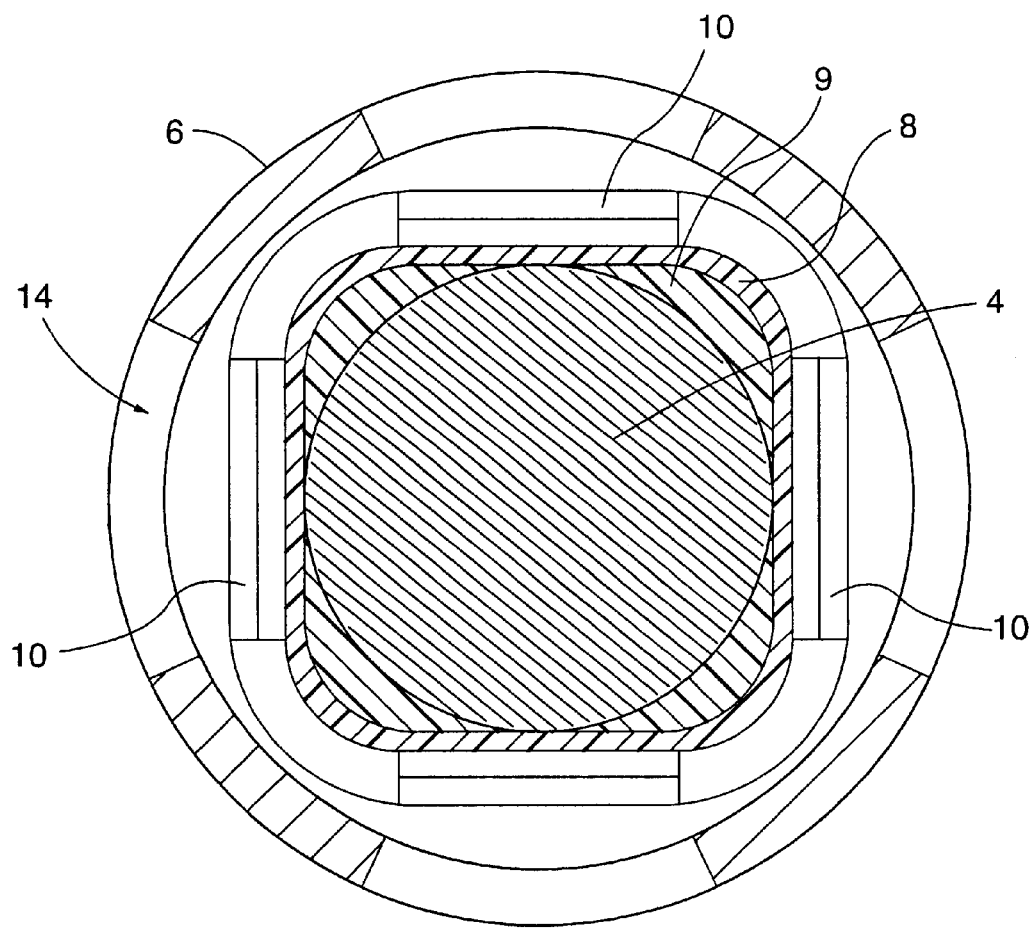
FIG. 3a illustrates the circuit board of FIG. 2 in a mounted state, where the radiation chips are facing outwards.

In FIG. 3a a cross section through a guide wire having attached thereto the device discussed above with reference to FIG. 1 and FIG. 2. The shown device comprises a core wire 4, around which a flexible support 8 having radiation chips 10 attached to it, is wrapped. Suitable glue or other adhesive material 9 is provided on the surface of the core wire 4 for attaching the flexible support 8. There is also provided a protective tube 6 having apertures or windows 14 in order not to hinder the radiation to exit properly. If the tube 6 is made of X-ray transparent material, of course no separate apertures are required.

Figure 3B:
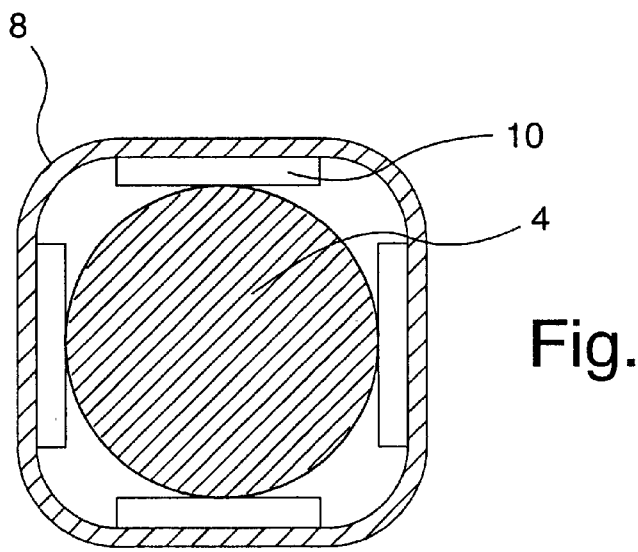
FIG. 3b shows the circuit board mounted in an inverted fashion compared to FIG. 3a, i.e. with the flexible circuit board facing outwards, thereby protecting the chips.

In FIG. 3b there is shown an inverted form of the device. Here the flexible support 8 is wrapped around the core wire 4 such that the radiation chips 10 are facing the surface of the core wire 4. This means that the flexible support also will act as a mechanical protection for the X-ray emitting chips.

Thus, the assembly shown in FIG. 2a, i.e. flexible support 8 having said chips 10 mounted thereon, is wrapped circumferentially around a core wire 4. The diameter of such a wire is of the order of 0.2–1 mm. Hence the width W of said support 8 should be of the order of 1.5–3 mm.

Of course the assembly could be mounted on some other support, such as a short piece of tube which in its turn may be threaded onto a guide wire. It is also conceivable to provide a rod like structure of a polymer material and to deposit a circuit pattern on said rod directly.

The radiation chips would then be surface mounted on said pattern. Thereby one manufacturing operation would be eliminated.

The chips 10 for the generation of radiation can have any suitable design, although preferred ones are disclosed in our copending U.S. provisional application serial No. 60/137, 478. However, for ease of understanding a chip will now be schematically described with reference to FIG. 5, wherein one possible embodiment is illustrated.

The radiation chip 40 of Fig. comprises a base member 42 having a depression 44 formed therein. The base member 42 can be made of silicon or any other material suitable for the purpose, such as semi-conductors, metals. An important property is that the materials should be possible to pattern using lithographic methods or depositing methods, i.e. in general methods applicable in the semi-conductor technology. The depression 44 may be provided by e.g. etching. On the bottom of the depression and in electrical contact with the base member 42 there is attached or provided a cathode 43. The cathode is provided as a large number of field emitting micro tips 45. These tips are either small, discrete tips, or can be formed by depositing a polycrystalline layer of e.g. diamond or diamond like material.

A cover member 48 is placed on the base member, optionally with a spacer member 46 of an insulating material provided between cover and base. On the inside of the cover 48 an anode layer 50 can be deposited.

The chip 40 is attached to a bond pad on the flexible sheet 8, such that the base member 42 is in electrical contact therewith.

In addition to the two ways of mounting the radiation assembly, namely with the flexible support facing outwards and the radiation chips facing inwards against the core wire, and the opposite respectively, there are two possible ways of attaching the chips to the support.

In a first variant the anode can be mounted so as to face the support, and in a second the cathode is facing the support. However, it will of course be mandatory to mount the radiation chips such that the radiation always radiates radially outwards. This means that for the embodiment where the chips are located on the surface of the assembly, as mounted on the core wire, the cathode must be facing the support, and for the embodiment where the support acts as a "wrapper" enclosing the chips, the anode must face the support. This can be clearly seen in FIGS. 3a and 3b.

What is claimed is:

1. A device for providing ionizing radiation at a therapy location inside a living body, comprising
    a core member (4; 11);
    a flexible support member (8) provided on the surface of said core member (4; 11);
    a miniaturized source (10) of ionizing radiation attached to said flexible support member (8); and
    coupling means (16a, 16b, 18) for coupling said sources of ionizing radiation to an external power source.

2. The miniaturized radiation source as claimed in claim 1, wherein said radiation source is integrated with a guide wire.

3. The miniaturized radiation source as claimed in claim 1, wherein said radiation source is integrated with a cannula.

4. The miniaturized radiation source as claimed in claim 1, wherein said radiation source is integrated with a catheter.

5. The miniaturized radiation source as claimed in claim 1, wherein the flexible support is provided with a circuit pattern comprising bond pads (16a, 16b) and conductor lines (18).

6. The miniaturized radiation source as claimed in claim 1, wherein the radiation source(s) comprise(es) a structure forming an X-ray source, having a cathode and an anode, coupled to said conductor lines and via said coupling means to said external power source.

7. The miniaturized radiation source as claimed in claim 1, wherein the number of miniaturized radiation sources is one to six, preferably two to four, most preferably four.

8. The miniaturized radiation source as claimed in claim 1, wherein the radiation sources are arranged symmetrically around the circumference of said core member.

9. The miniaturized radiation source as claimed in claim 1, wherein said radiation sources are provided in a plurality of rows each row having a plurality of radiation sources provided on said flexible support member.

10. The miniaturized radiation source as claimed in claim 1, comprising a control unit (3) having switching means for selectively energizing and de-energizing said radiation source(s).

11. The miniaturized radiation source as claimed in claim 1, providing X-ray radiation in the range of 5–30 keV.

12. The miniaturized radiation source as claimed in claim 1, wherein the X-ray sources are energizable individually or in groups.

13. The miniaturized radiation source as claimed in claim 12, wherein said chips are arranged in a staggered configuration.

14. A miniaturized radiation device, comprising
    a support member in the form of a flexible sheet;
    a circuit pattern of electrical contact pads and interconnecting conductor lines or leads provided on said support member; the pads being interconnected via said patterned lines;
    a plurality of radiation chips electrically connected to selected ones of said pads.

15. A miniaturized radiation device as claimed in claim 14, wherein all chips are individually energizeable at a desired voltage.

16. A miniaturized radiation device as claimed in claim 14, wherein said support member is of a material such as polyimide/kapton.

17. A miniaturized radiation device as claimed in claim 14, wherein said radiation chips are grouped together such that one group comprising two or more chips is connectable to one voltage source via said conductor lines, and another group is connectable to a second voltage source.

18. A miniaturized radiation device as claimed in claim 17, wherein said chips are grouped on said flexible support member in several rows and columns.

19. A miniaturized radiation device as claimed in claim 17, wherein said chips are arranged in a staggered configuration.

20. A miniaturized radiation device as claimed in claim 14, wherein there is provided a multiplexer on said support member, having two energizing/excitation leads and one data line, and a plurality of outputs for sequential energizing of said chips.

21. A device for providing ionizing radiation at a therapy location inside a living body, comprising
- a support member in the form of a flexible sheet;
- a circuit pattern of electrical contact pads and interconnecting conductor lines or leads provided on said support member; the pads being interconnected via said patterned lines;
- a plurality of radiation chips electrically connected to selected ones of said pads; and
- a core member on which said flexible support member is wrapped circumferentially.

* * * * *